United States Patent [19]
Stevens et al.

[11] Patent Number: 5,358,871
[45] Date of Patent: Oct. 25, 1994

[54] CULTURE VESSEL

[75] Inventors: Timothy A. Stevens, Madison; Edward F. Mussi, Hewitt; Douglas P. Henderson, Morristown; Tadeusz A. Tyndorf, Manalapan Township, Monmouth County, all of N.J.

[73] Assignee: Becton, Dickinson and Company, Franklin Lakes, N.J.

[21] Appl. No.: 105,830

[22] Filed: Aug. 12, 1993

Related U.S. Application Data

[63] Continuation-in-part of Ser. No. 3,774, Jan. 13, 1993.

[51] Int. Cl.$^5$ .............................................. C12M 3/06
[52] U.S. Cl. .................................... 435/284; 435/297; 435/298; 435/299; 435/301; 435/311; 422/101; 422/102
[58] Field of Search ............... 422/101, 102, 104; 435/284, 285, 286, 297, 298, 299, 300, 301, 310, 311, 287, 296; 210/321.84, 239, 249, 250, 348, 460, 463, 470, 471, 473, 476, 482

[56] References Cited

U.S. PATENT DOCUMENTS

| | | | |
|---|---|---|---|
| 4,495,289 | 1/1985 | Lyman et al. | 435/284 |
| 4,657,867 | 4/1987 | Guhl et al. | 435/284 |
| 4,871,674 | 10/1989 | Matsui et al. | 435/284 |
| 5,026,649 | 6/1991 | Lyman et al. | 435/284 |

FOREIGN PATENT DOCUMENTS

0483620 10/1990 European Pat. Off. ....... B01L 3/00

*Primary Examiner*—Jeffrey R. Snay
*Attorney, Agent, or Firm*—Nanette S. Thomas

[57] ABSTRACT

Apparatus for growing cells or tissue in vitro and for supporting, positioning and/or centering cell culture inserts that are used in such procedures. The apparatus comprises a body with a plurality of wells wherein a cell culture insert may be supported and centered without interfering with the growing of tissue culture in vitro.

10 Claims, 11 Drawing Sheets

CULTURE VESSEL

This application is a continuation-in-part of U.S. Ser. No. 08/003,774, filed on Jan. 13, 1993.

BACKGROUND OF THE INVENTION

1. Field of the Invention

This invention relates to an apparatus useful for procedures in growing cells or tissue culture in vitro and more particularly for supporting, positioning and/or centering cell culture inserts that are used in the procedures.

2. Description of the Related Art

Culture vessels are described in U.S. Pat. Nos. 4,495,289 and 5,026,649 and European Patent Application No. 0 483 620 A2. Culture vessels comprise wells which generally have a circular shape and size which permits the introduction therein of a cell culture insert having a membrane upon which cell attachment, growth and differentiation occur. The culture vessels containing the wells are typically rectangular and have a standard size in order to accommodate standard analytical apparatus.

Conventional cell culture inserts used in culture vessels are described in U.S. Pat. Nos. 4,871,674 and 5,026,649. U.S. Pat. No. 4,871,674 discloses a cell culture insert which comprises discontinuous projecting parts for hanging the cell culture insert on an upper circumferential part of the culture vessel. U.S. Pat. No. 5,026,649 discloses a cell culture insert which comprises a projecting part for hanging the culture cell on an upper circumferential part of the culture vessel, and further includes openings in the sidewalls for exchanging gas and for pipeting sample.

Although there are a number of culture vessels and cell culture inserts commercially available and described in patent publications, it is believed that there are no culture vessels or cell culture inserts available that can be used together to support, position and/or center a cell culture insert without interfering with the growing of tissue cultures in vitro.

SUMMARY OF THE INVENTION

The present invention is a device for growing cells or tissue culture in vitro. The device comprises a body with wells shaped to accommodate an insert, such as a cell culture insert.

The device preferably comprises a test plate including an upper surface, a lower surface, and a plurality of wells. Each well is substantially disposed between the upper and lower surface of the test plate. Each well comprises a sidewall, a bottom surface and a raised mouth surface. Most preferably, the raised mouth surface of each well includes a means for supporting a cell culture insert. This memos is desirably raised from the upper surface.

The raised mouth surface preferably includes means for positioning and/or centering a cell culture insert. The preferred means is at least one integral lip portion extending from the raised mouth surface. The integral lip portion may be arranged to assist in positioning and/or centering a cell culture insert without limiting the movement of the cell culture insert.

Desirably, the cell culture insert that may be used with the device comprises an upper portion, a lower portion and sidewalls extending from the upper portion to the lower portion. The lower portion includes a bottom surface which may have attached thereto a flat permeable membrane. The upper portion includes a top surface which carries at least one outwardly extending flange. The flange allows the cell culture insert to be supported on the top surface of the well of the device so that there is clearance between the bottom of the membrane and the bottom surface of the well. The clearance provides a controlled static head and diffusion for the fluid in the device so that cells can be properly cultured.

The cell culture insert may further include at least one support footing on the bottom surface. The footing may provide a degree of clearance between the membrane and the bottom surface of the well.

Most preferably, the outer surface of the sidewall of the cell culture insert may further include means for restricting and/or preventing the flange of the cell culture insert from falling into the well of the device.

Although the device of the present invention may be configured in a circle with one well, the preferable form of the device is a multi-sided structure with wells in an ordered array of parallel rows. Furthermore, the integral lip portions on the raised mouth surface of each well may be positioned so that the integral lip portion of one well does not face an integral lip portion of an adjacent well. This positioning of the integral lip portions assures that the flanges of adjacent cell culture inserts positioned in the wells can be accessible, do not contact one another and that the cell culture insert may be aseptically placed and removed into or out of the well of the device.

The device may further include a removable lid which can be positioned over the upper surface. The lid includes a top wall and a peripheral skirt that extends from the top wall. The lid serves to prevent the loss of sample from the well interior, to protect the contents of the device from the environment and to protect the user from the contents of the device should it contain a harmful or potentially harmful material.

The device preferably receives a cell culture insert in the well. The cell culture insert is positioned into the well wherein the flanges of the cell culture insert are supported on the raised mouth surface of the well and located between the integral lip portions. The integral lip portions assist in substantially positioning and/or centering the cell culture insert in the well and the raised mouth surface of the well substantially restricts the cell culture insert from falling into the well. Movement of the cell culture insert within the well may be such that the cell culture insert wall and the well sidewall can touch at one or more locations.

Alternatively, the upper mouth surface of the well may comprise at least one integral standing rib portion and the flange of the cell culture insert may comprise a slot to engage the standing rib portion. In this embodiment, the cell culture insert is positioned in the well wherein the slot of the flange engages the integral stranding rib portion of the well. The rib portion assists in substantially positioning and/or centering the cell culture insert in the well while movement of the cell culture insert in the well may be such the cell culture insert wall and the side wall of the well can touch at one or more locations.

The exterior dimensions of the portion of the cell culture insert within the well of the device are sufficiently less than the well diameter to allow a pipet or similar device to be positioned in the space between the well of the device and the cell culture insert for fluid filling or aspiration without disturbing or removing the cell culture insert from the well of the device. The space allows the pipet to reach the bottom of the well and introduce or remove medium from beneath the membrane and about the outer surface of the sidewall of the cell culture insert without contaminating the upper surface of the membrane.

The device and related removable lid may be formed in different sizes and geometric configurations so as to be used with different size and geometric configured cell culture inserts. The removable lid may be formed to be positioned over the upper surface of the device in one orientation so as to reduce cross contamination between the wells in the event the lid is repositioned over the upper surface of the device. The device and the removable lid are preferably made of an optically clear plastic to facilitate viewing of the wells and cell culture inserts.

An important feature of the present invention is that in a multi-well configuration, flange to flange contact between the cell culture inserts is prevented so as to reduce contamination. This is accomplished due to the orientation of the integral lip portions on each well wherein the integral lip portion of one well does not face or interfere with an integral lip portion of an adjacent well.

A further feature of the present invention is that the top surface configuration of the well of the device may facilitate the aseptic placement and removal of the cell culture insert into or out of the well of the device with tweezers or forceps, as well as providing support to the cell culture insert when placed in the well of the device.

DETAILED DESCRIPTION

Figure 1:
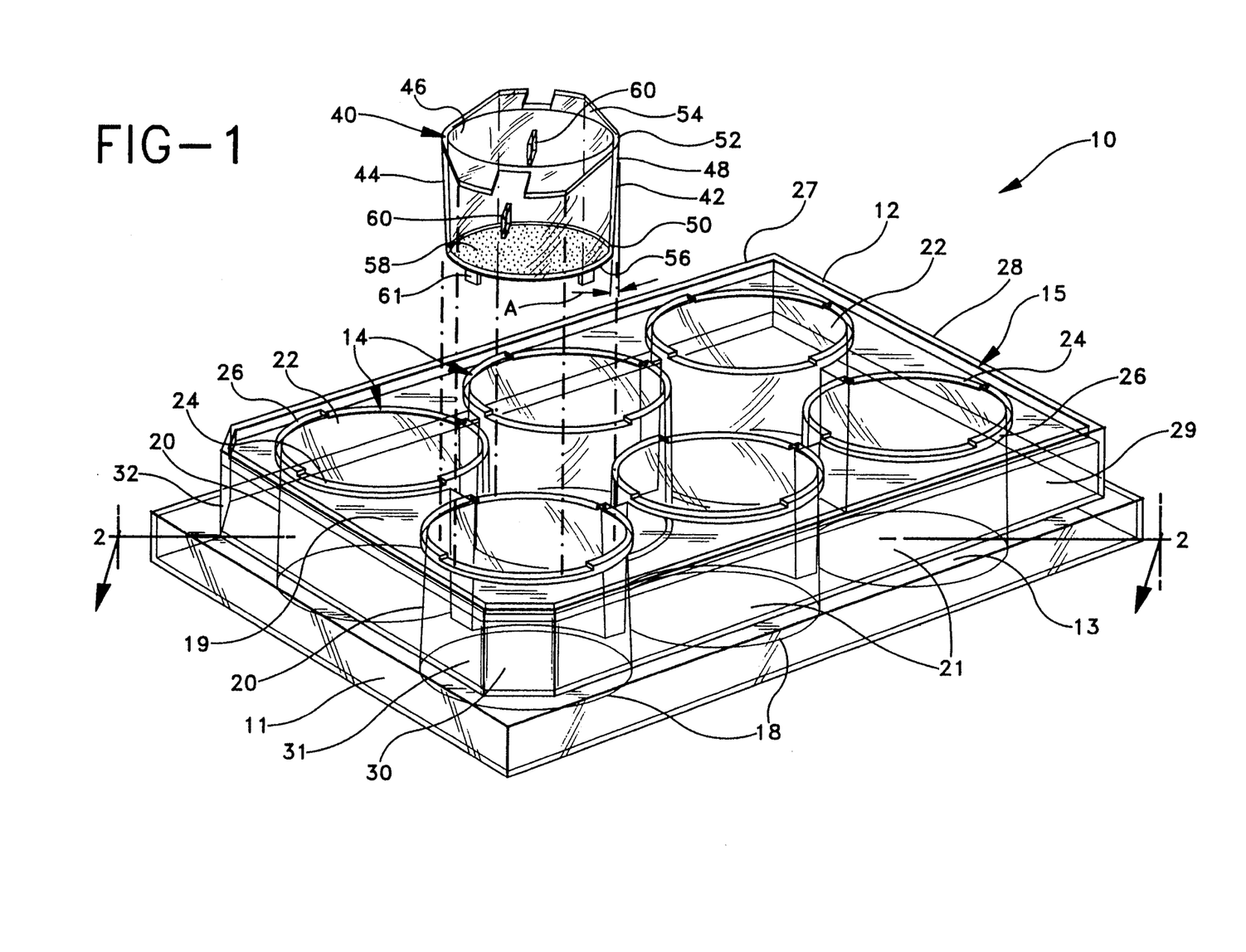
FIG. 1 is an exploded perspective view of a multi-well culture vessel and a cell culture insert.

An apparatus 10 for growing tissue cultures as shown in FIG. 1 includes a culture vessel 15 and a cell culture insert 40. Although a six well culture vessel is shown, it should be appreciated that the culture vessel may have one, eight, twelve, twenty-four or some other number of wells selected for the particular purpose for which the apparatus system is used.

Figure 2:
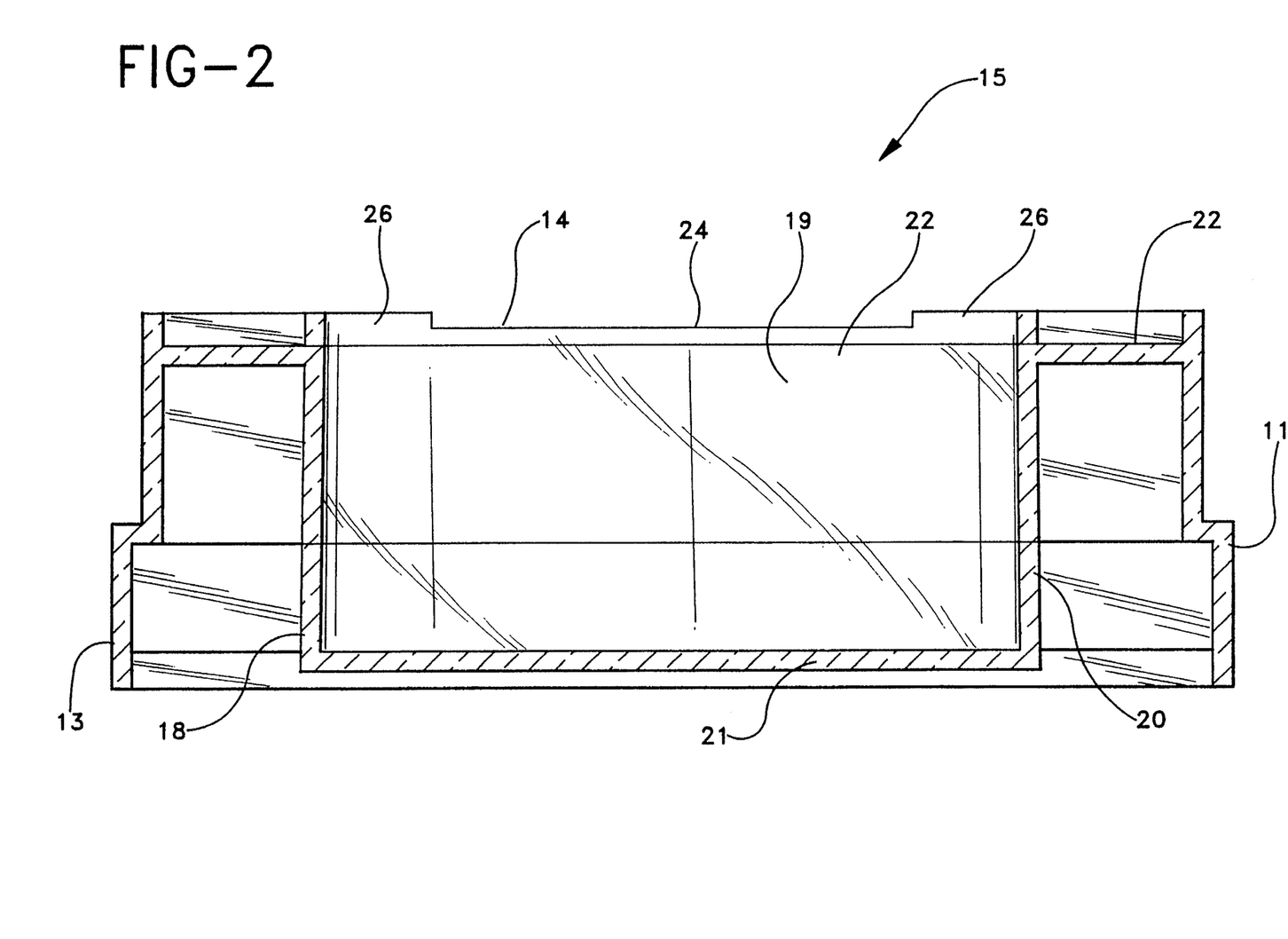
FIG. 2 is a cross sectional view taken along lines 2—2 of FIG. 1 illustrating the means available for supporting, positioning and/or centering a cell culture insert in the well of a culture vessel.

As shown in FIGS. 1 and 2, culture vessel 15 includes a base 11 with an upper surface 12 and lower surface 13. The culture vessel further includes a number of wells 14 each comprising a sidewall 20 extending from the upper surface to the lower surface. A top portion 19 of the well comprises an open end 22, a top surface 24 extending from the upper surface and two integral lip portions 26 extending from the top surface. A bottom portion 18 of the well comprises a closed end 21.

Base 11, as illustrated in FIG. 1, typically is transparent and may be molded, for example, of polyvinylchloride or polystyrene. The culture vessel further includes sidewalls 27, 28, 29, 30, 31 and 32 that extend from upper surface 12 to lower surface 13. Sidewalls 27 and 29, and 28 and 31 are substantially parallel to each other respectively. Sidewall 30 is located between sidewalls 29 and 31 and sidewall 32 is located between sidewalls 31 and 27.

As shown in FIG. 1, the cell culture insert includes a body wall 42 having an outer wall surface 44 and an inner wall surface 46. Body wall 42 extends from an upper portion 48 to a lower portion 50. The body wall may taper from the upper portion to the lower portion. Although it is within the purview of this invention that draft angle A of the cell insert be from about 5 degrees to about 8 degrees, it is most preferred that the draft angle is 6 degrees. Upper portion 48 comprises a top surface 52 which carries two outwardly extending flanges 54. The flanges are located opposite from one another approximately 180° apart and are discontinuous. Flanges 54 comprise a horizontal orientation for resting on top surface 24 of well 14.

Lower portion 50 comprises a bottom surface 56 to which a microporous membrane 58 is adhered. The membrane may be made of suitable material including, but not limited to, perforated inert film, hydrated gel, or a layered combination.

In the embodiment illustrated, two projecting or extending tabs 60 are located on outer wall surface 44 of the cell culture insert. The tabs are located opposite from one another or approximately 180° apart and approximately half the distance between the upper and lower portions. The projecting tabs provide stability to the cell culture insert when it is in the well and shifted for pipette insertion. In the event the cell culture insert is shifted and one of the flanges falls into the well, the projecting tabs will substantially prevent the opposite flange from falling into the well.

The cell culture insert may further include feet or supports 61 located on the bottom surface. The feet are located opposite from one another or approximately 180° apart. Feet 61 are used when the extending flanges do not provide adequate support to the cell culture insert in a particular well configuration. It is most desirable that a space be maintained between the membrane on the bottom surface of the cell culture insert and the well of the culture vessel so that cells may be cultured on both sides of the membrane. Feet 61 further provide support to the cell culture insert when placed on a flat surface.

Figure 3:
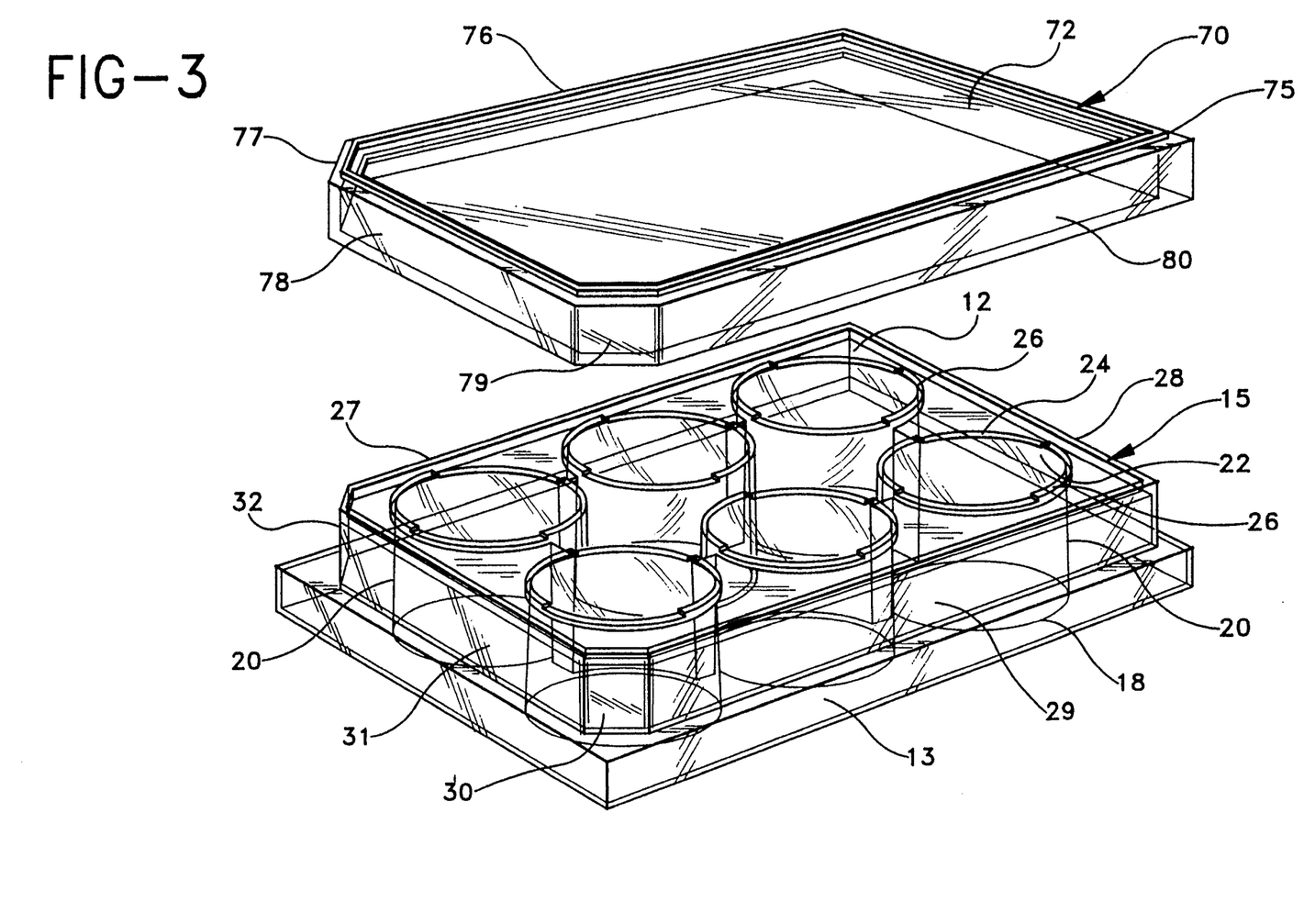
FIG. 3 is an exploded perspective view of a multi-well culture vessel and the optional removable lid not attached.

As shown in FIG. 3, the apparatus further includes a removable lid 70. Removable lid 70 includes a top wall 72, and peripheral sides 75, 76, 77, 78, 79 and 80 that extend from the top wall. The lid removably covers the upper surface of the culture vessel wherein the peripheral sides abut closely with the base of the culture vessel. In particular peripheral sides 77 and 79 of the lid abut with sidewalls 30 and 32 of the culture vessel. The lid is configured so that peripheral sides 77 and 79 are tinable to abut with sidewalls 27, 28, 29 and 31 of the culture vessel. Therefore the lid may only be mated with the culture vessel in one way so that cross contamination is minimal between the wells of the culture vessel.

Figure 4:
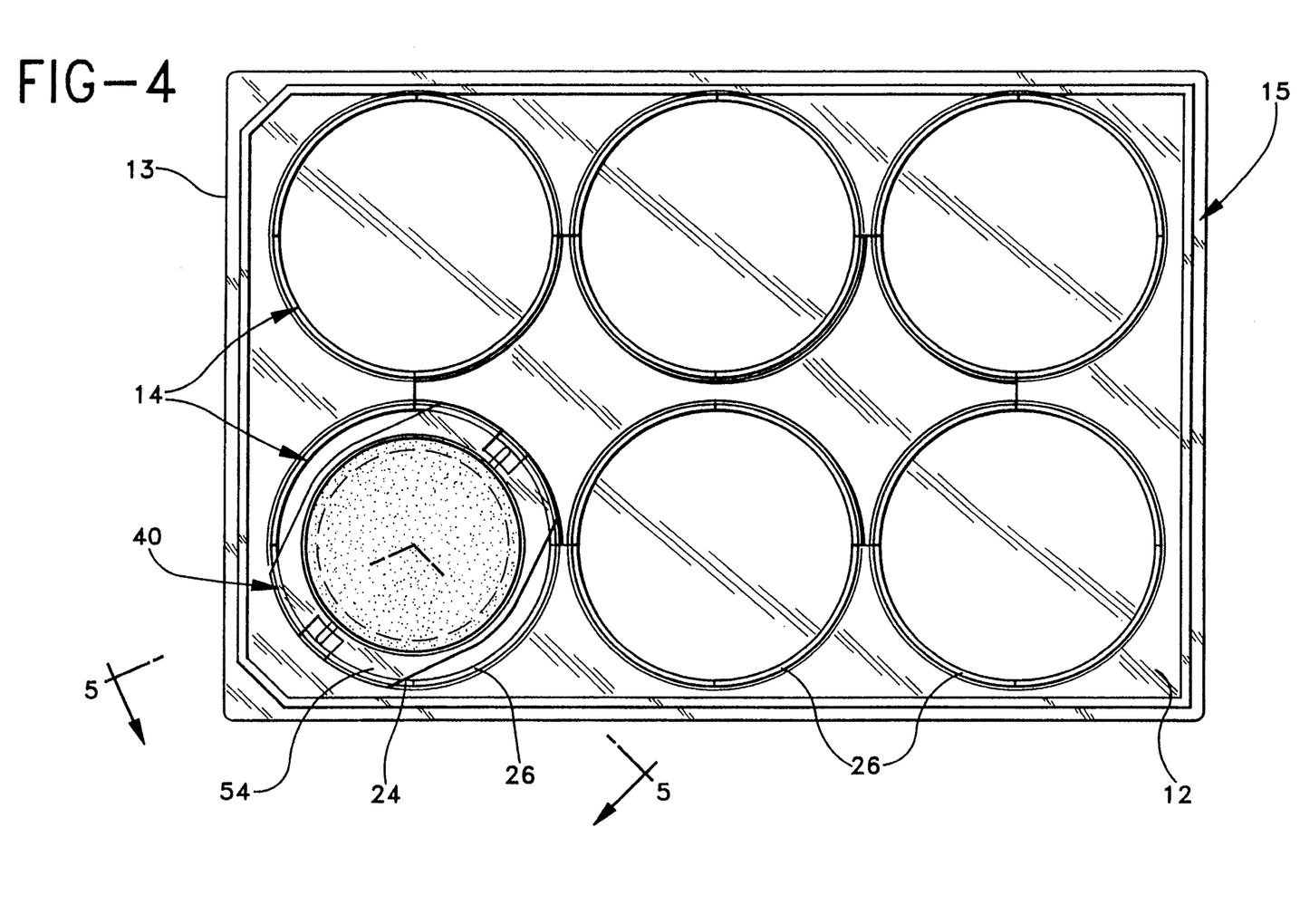
FIG. 4 is a top view of FIG. 1 illustrating the cell culture insert supported in the well of a culture vessel.

As shown in FIG. 4, wells 14 are sufficiently spaced from one another and the integral lip portions are oriented so as not to face or interfere with the integral lip portions of adjacent wells. The integral lip portions of each well are located opposite from one another or approximately 180° apart. This particular orientation of the integral lip portions substantially prevents flange to flange contact between the cell culture inserts and substantially reduces cross contamination between the cell culture inserts.

Figure 5:
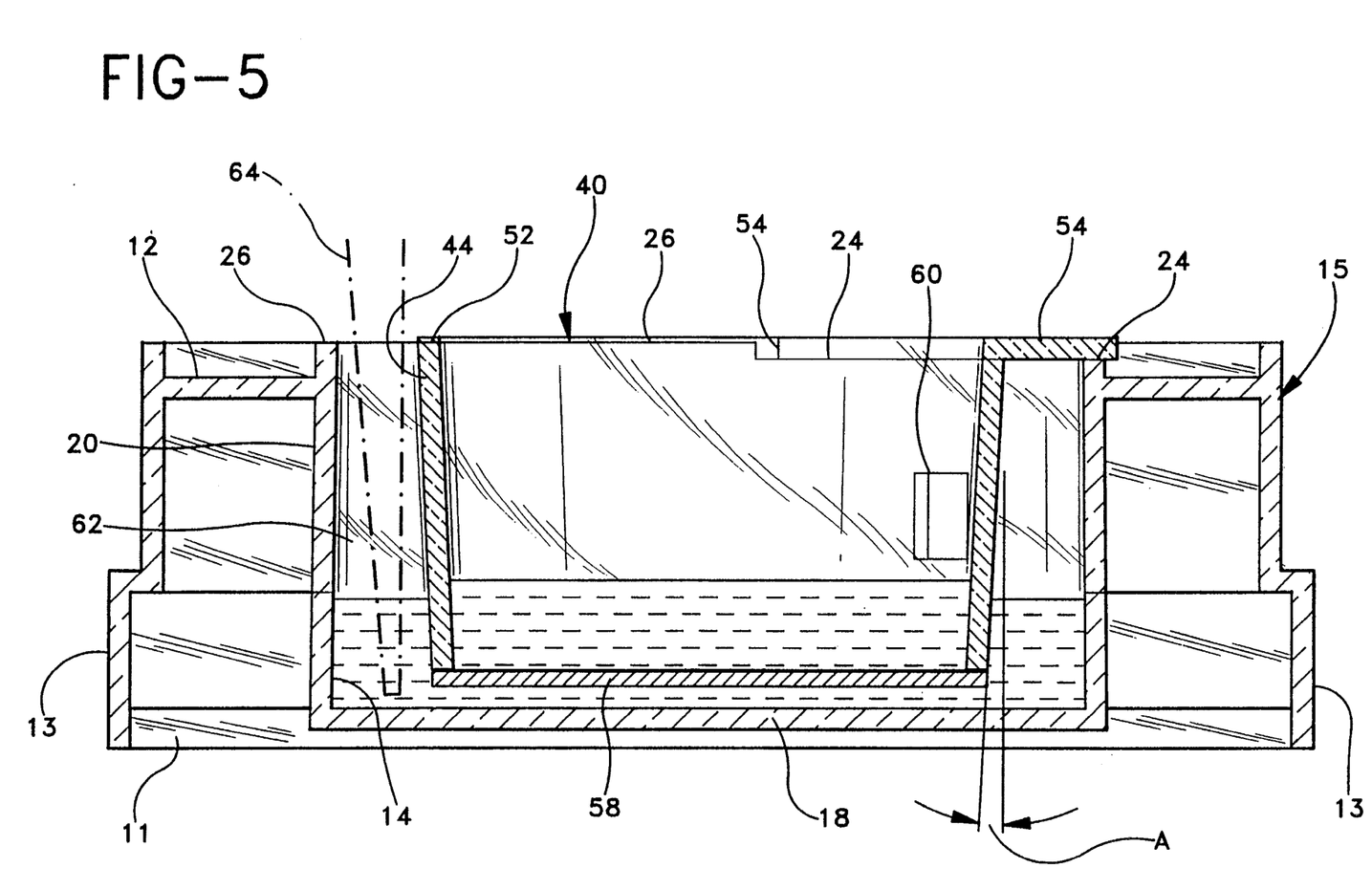
FIG. 5 is a cross-sectional view taken along lines 5—5 of FIG. 4 illustrating where a pipet tip, shown in phantom, may enter the space between the cell culture insert and the well of the culture vessel.

FIG. 5 illustrates the orientation of the cell culture insert as supported in culture vessel 15 wherein flange 54 is positioned on top surface 24 and between integral lip portions 26. Top surface 24 supports the cell culture insert and integral lip portions 26 assist in positioning and/or centering the cell culture insert without limiting movement of the cell culture insert. FIG. 5 also illustrates a pipet tip 64, in phantom, which enters the space 62 between outer wall surface 44 of the cell culture insert and sidewall 20 of the culture vessel.

The centering feature provided by integral lip portions 26 can be seen in FIG. 5. Cell culture insert 40 is set within well 14 and spaced sufficiently from well sidewall 20 as facilitated by top surface 24 and integral lip portions 26. Thus, capillary action should not occur to cause solution or media in space 62 from wicking up outer surface 44 and entering the interior of the cell culture insert or spilling from well 14. The movement of the cell culture insert, however, may be such that the cell culture outer wall surface and the sidewall of the well can touch at one or more locations.

The invention, as shown in FIGS. 6–11 includes many components which are substantially identical to the components of FIGS. 1–5. Accordingly, similar components performing similar functions will be numbered identically to those components of FIGS. 1–5, except that a suffix "a" will be used to identify those similar components in FIG. 6–11.

Figure 6:
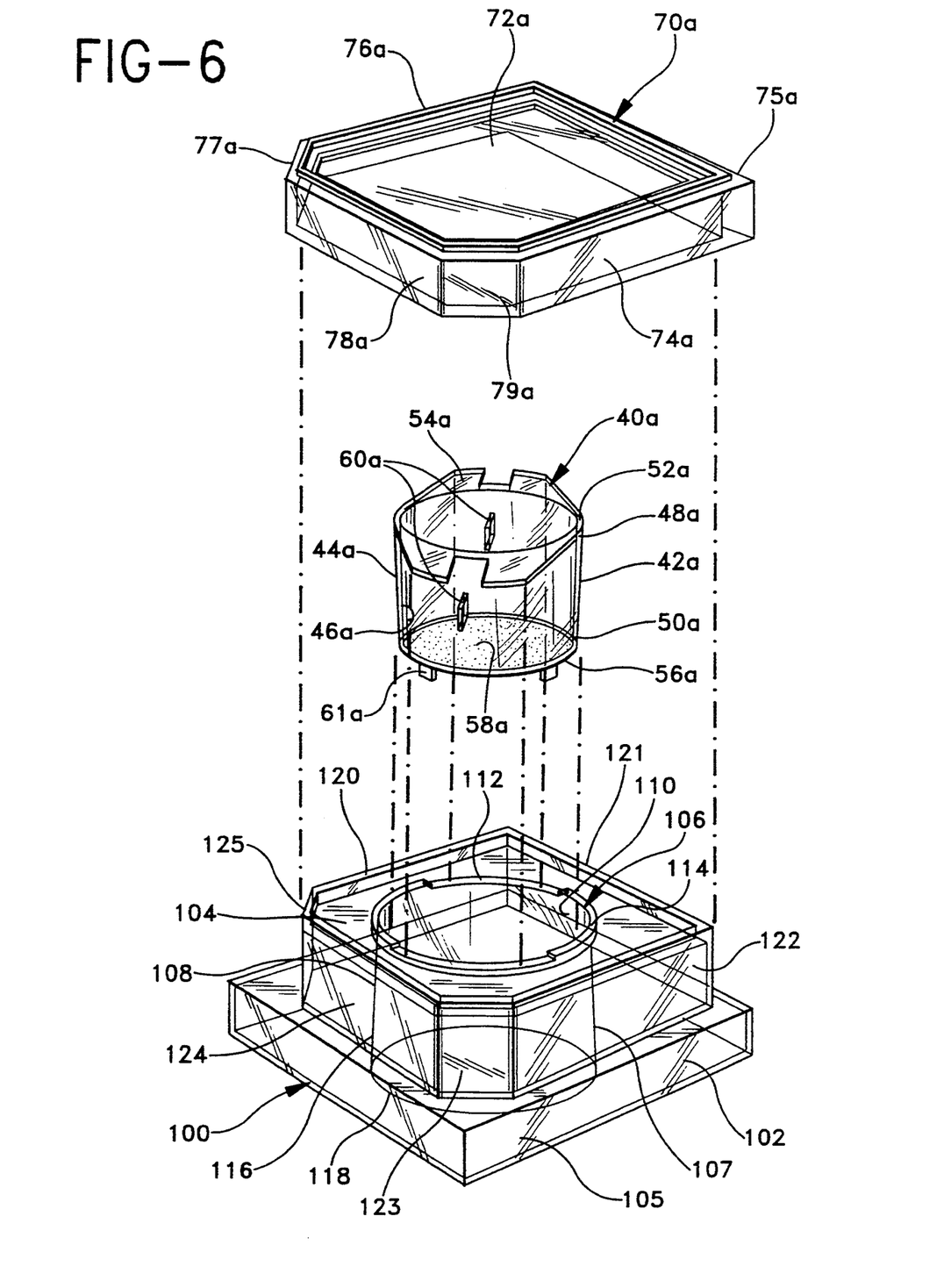
FIG. 6 is an exploded perspective view of an alternate embodiment of the present invention, a one-well culture vessel.

As illustrated in FIG. 6, a further embodiment of the invention includes a one well apparatus 90 having a culture vessel 100, a cell culture insert 40a and a removable lid 70a. The culture vessel includes a base 102 with an upper surface 104 and a lower surface 105. A well 106 comprising a sidewall 107 extends from the upper surface to the lower surface. A top portion 108 of the well comprises an open end 110, a top surface 112 extending from the upper surface and two integral lip portions 114 extending from the top surface. A lower portion 106 of the well comprises a closed end 118.

Base 102 typically is transparent and may be molded, for example, of polyethylene terephthalate. The culture vessel further includes sidewalls 120, 121, 122, 123, 124 and 125 that extend from upper surface 104 to lower surface 105.

Figure 7:
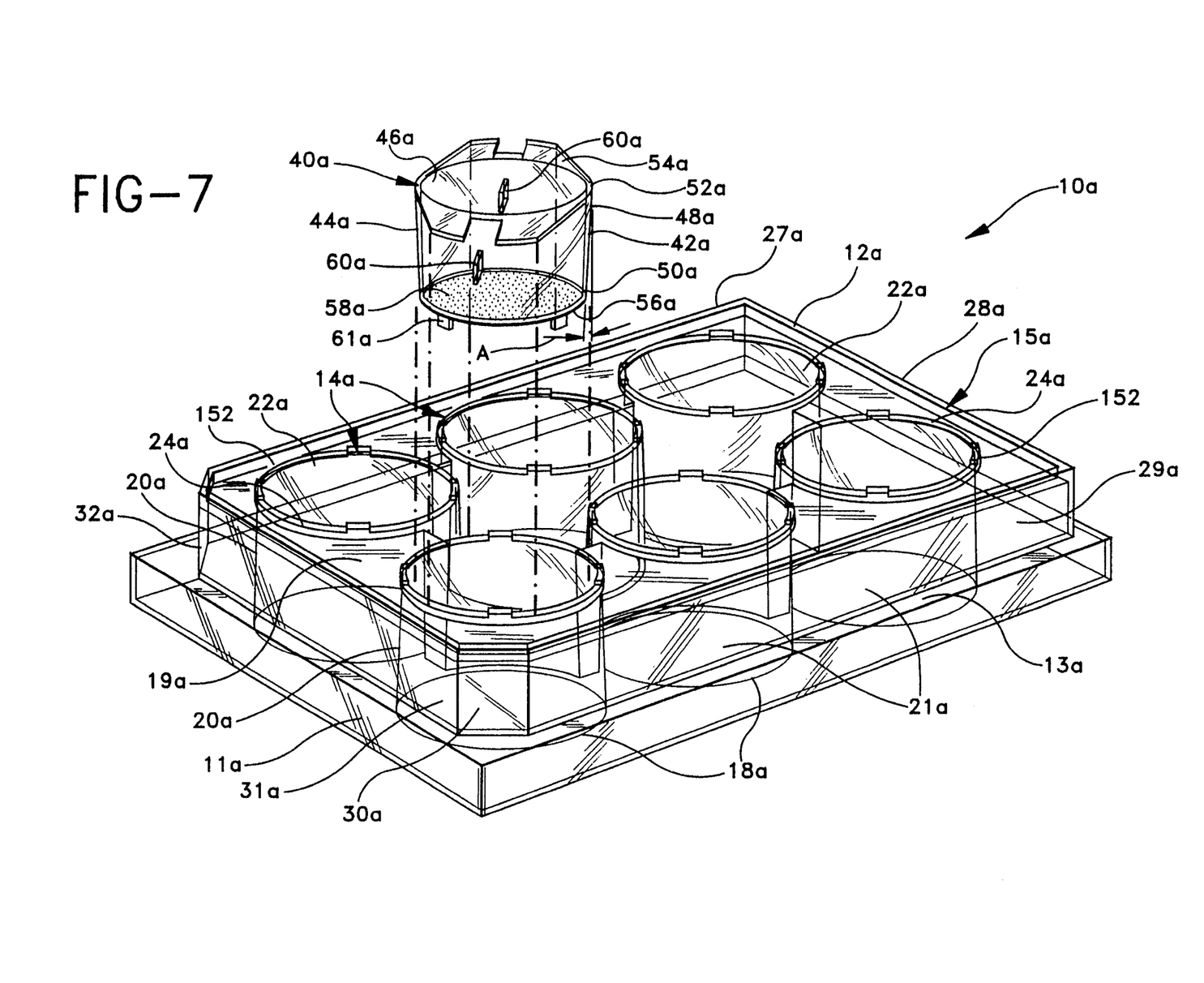
FIG. 7 is an exploded perspective view of a multi-well culture vessel and a cell culture insert similar to FIG. 1 illustrating an additional embodiment of the invention.
Figure 8:
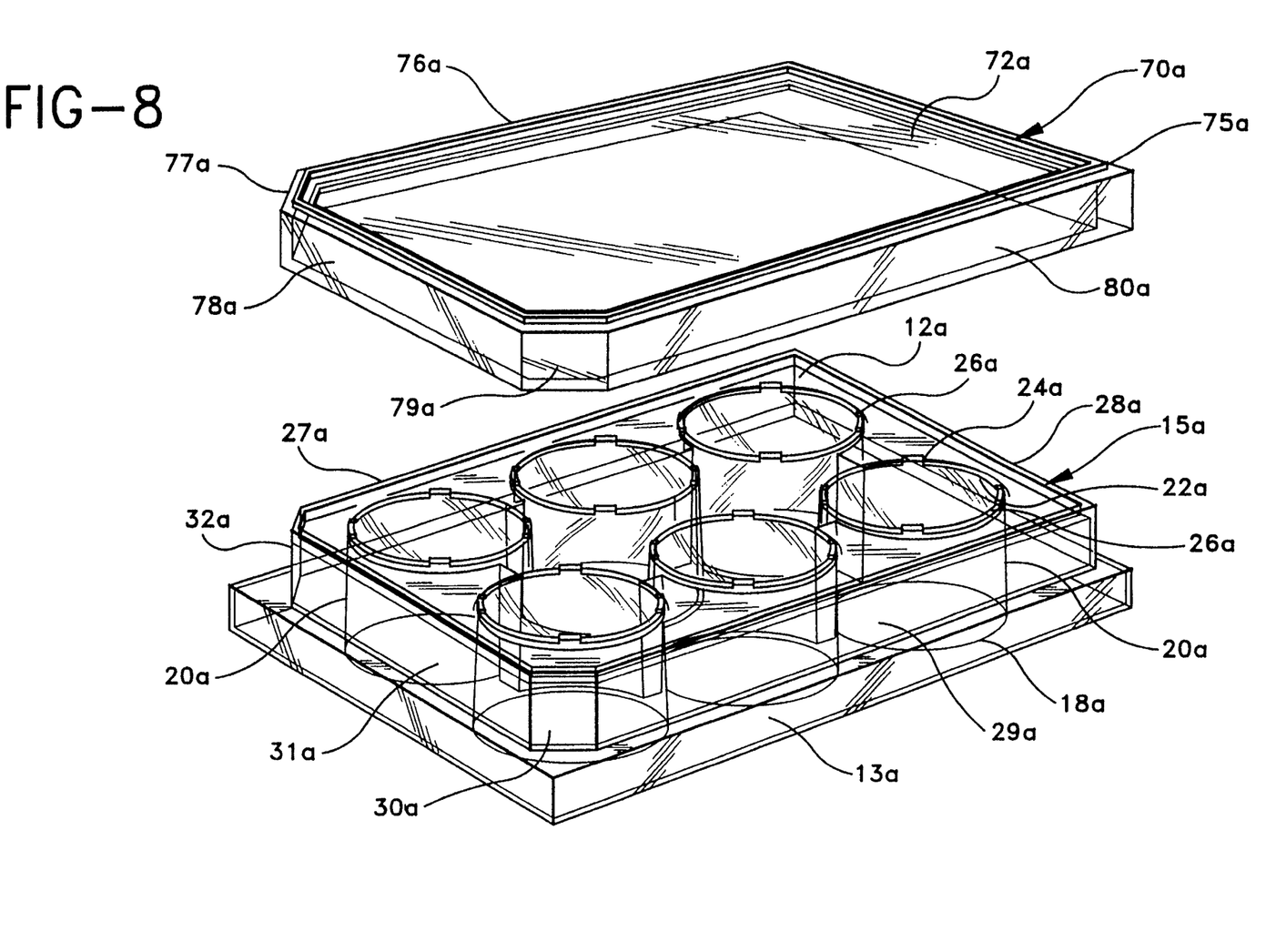
FIG. 8 is an exploded perspective view of the multi-well culture vessel of FIG. 7 and the optional removal lid not attached.
Figure 9:
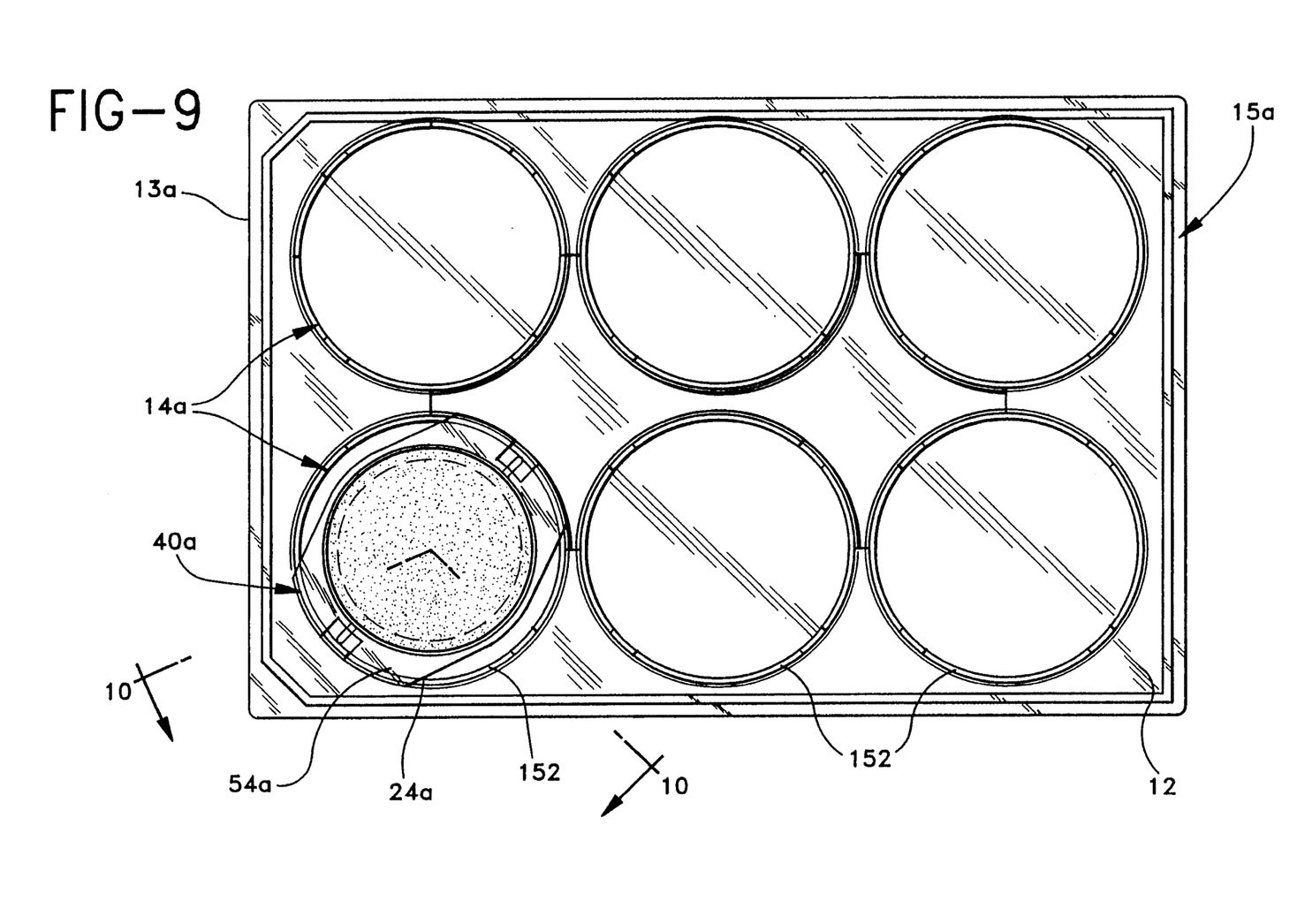
FIG. 9 is a top view of FIG. 7 illustrating the cell culture insert supported in the well of a culture vessel.

As illustrated in FIGS. 7–9, a further embodiment of the invention includes a culture vessel 15a wherein the top portion 19a of the well comprises two integral standing ribs portions 152 extending from top surface 24a and a modified cell culture insert 40a wherein each flange has a slot 156 to engage standing rib portions 152. The flanges are located opposite from one another approximately 180° apart and have a horizontal orientation for resting on top surface 24a of the well. Although it is within the purview of this invention that body wall 42a of cell culture insert 40a extends from upper portion 48a to lower portion 50a, it is most preferred that body wall 42a tapers from upper portion 48a to lower portion 50a. Although it is within the purview of this invention that draft angle A of the cell insert be from about 5 degrees to about 8 degrees, it is most preferred that the draft angle is 6 degrees.

Figure 10:
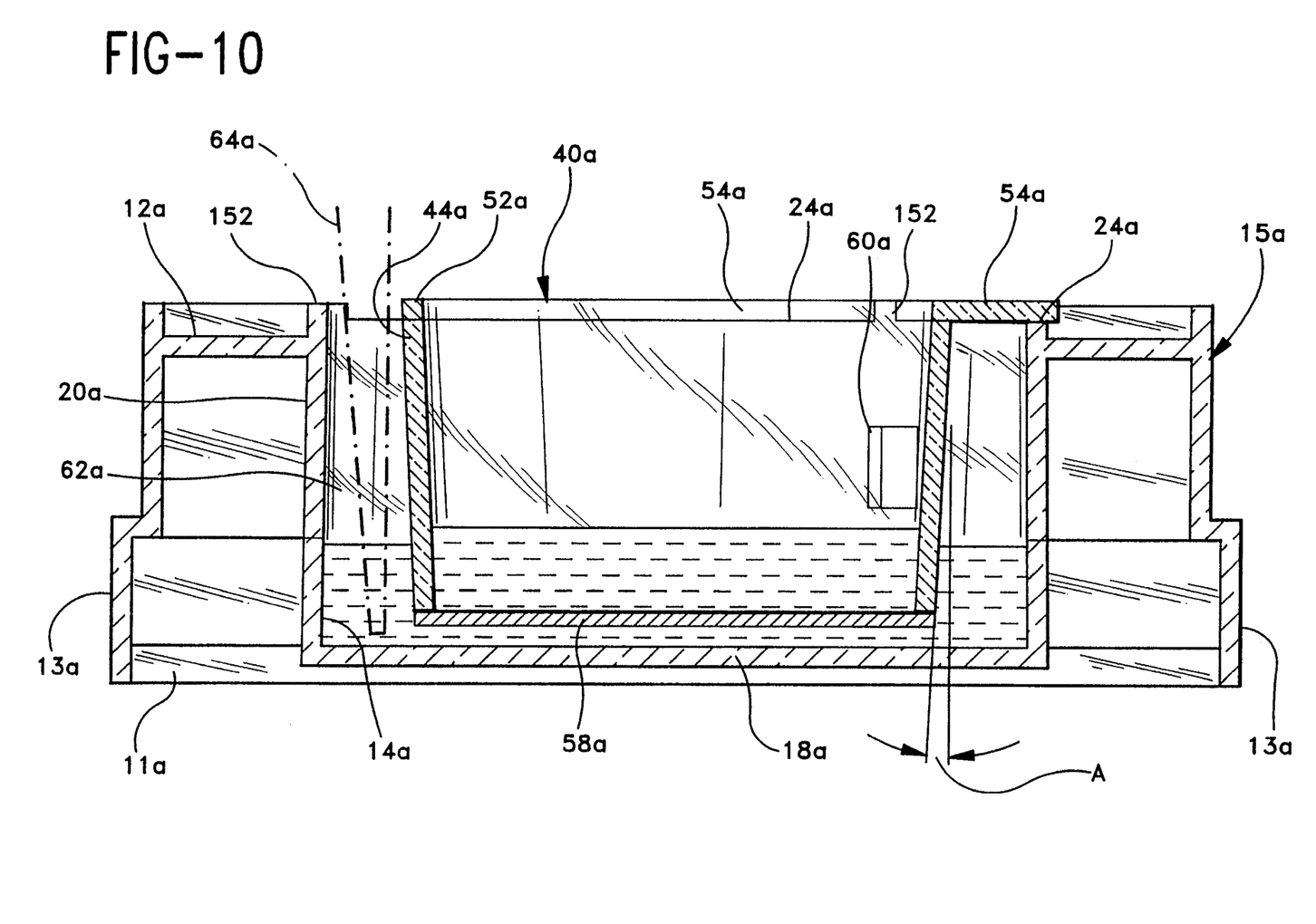
FIG. 10 is a cross-sectional view taken along lines 10—10 of FIG. 9 illustrating where a pipet tip, shown in phantom, may enter the space between the cell culture insert and the well of the culture vessel.

FIG. 10 illustrates the orientation of the cell culture insert as supported in culture vessel 15a wherein slot 156 of the flange engages integral standing rib 152. Top surface 24a supports the cell culture insert and the integral standing ribs assist in positioning and/or centering the cell culture insert.

Figure 11:
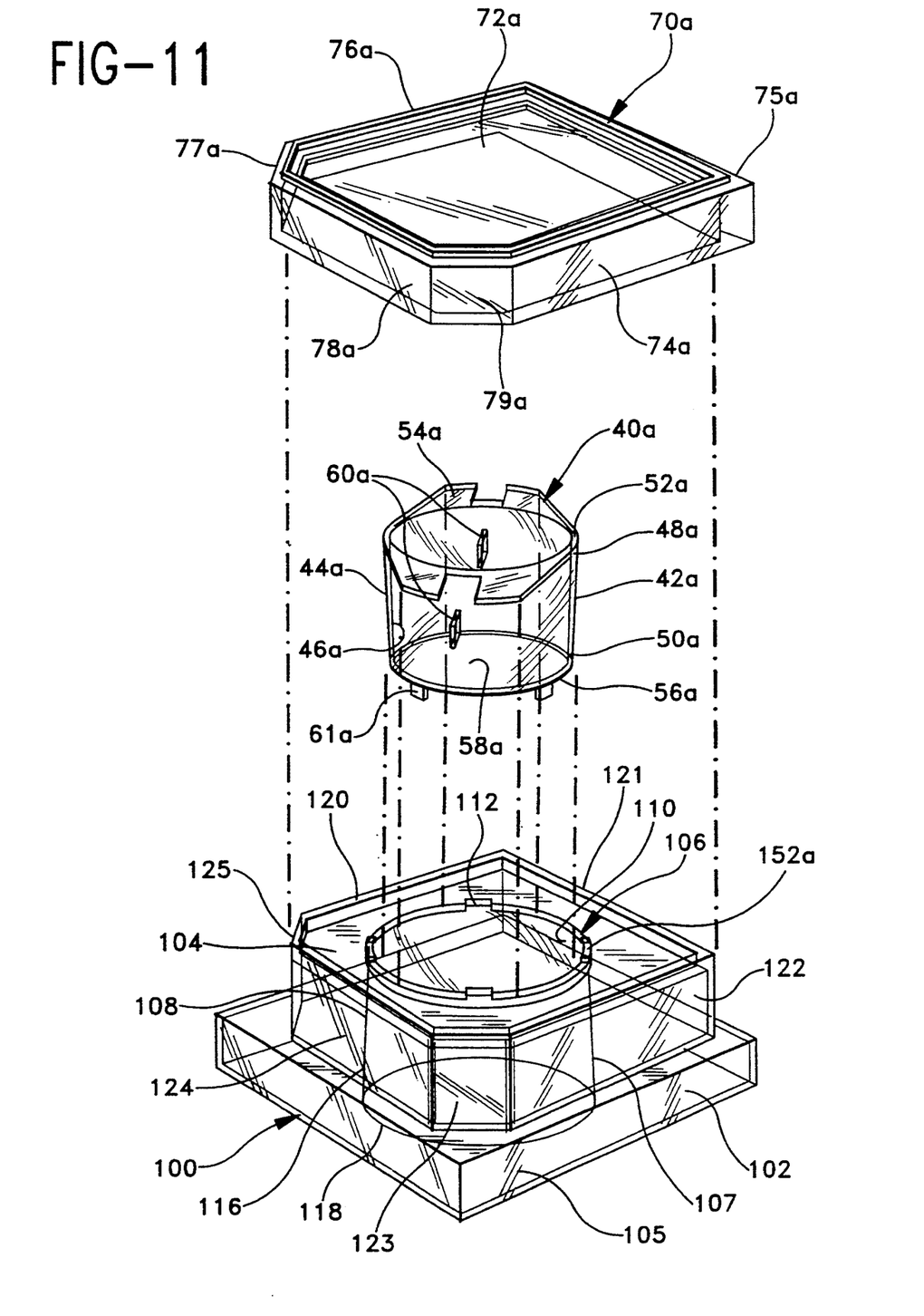
FIG. 11 is an exploded perspective view of a one-well culture vessel similar to FIG. 7, illustrating an additional embodiment of the invention.

FIG. 11 illustrates an additional embodiment of the invention, a one well apparatus.

As practitioners-in-the-art will understand, the culture vessel and cell culture insert of the present invention may be comprised of simple moldable parts which may be mass produced from a variety of materials, including, for example, polyethylene, polystyrene, polyethylene terephthalate, and polypropylene. As will be understood further by practitioners in the art, materials should be selected which provide a small degree of resiliency for the purpose of providing ease of insertion of the cell culture inserts into the culture vessel and ease of use for subsequent examination of the developed cultured cells.

What is claimed is:

1. Apparatus for use in growing tissue cultures in vitro comprising:

a culture vessel comprising an tipper surface, a lower surface, a plurality of wells extending from said upper surface to said lower surface, a raised mouth surface extending from each said upper surface of each well, and at least one projecting portion extending from each said raised mouth surface; and a cell culture insert suspended in one of said wells and comprising an upper portion, a lower portion, a sidewall comprising an inner and outer surface and extending from said upper portion to said lower portion, a permeable membrane attached to said lower portion and a flange comprising a slot extending from said upper portion for engaging with said projecting portions of said culture vessel.

2. The apparatus of claim 1 wherein said at least one projecting portion includes two projecting portions extending from each said raised mouth surface and being located opposite from one another.

3. The apparatus of claim 2 wherein said cell culture insert further comprises means for restricting movement of said cell culture insert in said one of said wells of said culture vessel extending from said outer surface of said sidewall.

4. The apparatus of claim 3 wherein said means for restricting movement of said insert includes two projecting tabs located opposite one another on the outer surface of said sidewall and between said upper portion and said lower portion.

5. The apparatus of claim 4 wherein said culture vessel is substantially rectangular in shape and said wells are in an ordered array of substantially parallel rows.

6. The apparatus of claim 5 further comprising a plurality of said cell culture inserts.

7. The apparatus of claim 6 wherein said projecting portions of the wells are in an ordered array to substantially prevent the flange of one cell culture insert from contacting the flange of another cell culture insert.

8. The apparatus of claim 7 further comprising a removable lid having a top wall and a peripheral skirt that extends from said top wall.

9. The apparatus of claim 8 wherein the sidewall of each of said cell culture inserts further comprises a draft angle from about 5 degrees to about 8 degrees.

10. The apparatus of claim 9 wherein said draft angle is about 6 degrees.

* * * * *